United States Patent [19]

Healy, Jr. et al.

[11] Patent Number: 4,816,410
[45] Date of Patent: Mar. 28, 1989

[54] CONTROL SLIDE FOR IMMUNOASSAY KIT AND METHOD OF MAKING SAME

[75] Inventors: Stephen F. Healy, Jr., Miami; Michael L. Rice, North Miami Beach; Martin L. Golick, Miami, all of Fla.

[73] Assignee: Coulter Corporation, Hialeah, Fla.

[21] Appl. No.: 925,617

[22] Filed: Oct. 29, 1986

[51] Int. Cl.⁴ ............................................. G01N 31/00
[52] U.S. Cl. ........................................... 436/10; 436/8
[58] Field of Search ......................................... 436/8–18, 436/508, 804, 805, 808; 424/3; 435/240, 262, 273, 6, 7, 810; 156/351, 57, 357, 363, 364, 556

[56] References Cited

U.S. PATENT DOCUMENTS 4,493,821  1/1985  Harrison ............................. 436/18
4,557,903 12/1985  McCormick ....................... 422/102
4,640,897  2/1987  Leynadier et al. .................. 436/18

Primary Examiner—Barry S. Richman
Assistant Examiner—T. J. Wallen
Attorney, Agent, or Firm—Myron C. Cass

[57] ABSTRACT

A control slide for use in an immunoassay having a section of a cell pellet retained on the slide in a stable and substantially permanent formation which can be stored at room temperature. Further, the invention includes the method of making the control slide.

4 Claims, 2 Drawing Sheets

CONTROL SLIDE FOR IMMUNOASSAY KIT AND METHOD OF MAKING SAME

This invention is concerned with control slides used in immunoassays and more particularly, relates to a novel control slide for use in an immunoassay wherein an intact cell specimen preferably will serve as the control medium. Further, the invention relates to a method of making the control slide.

BACKGROUND OF THE INVENTION

The immunoassay of the type which the invention is concerned is exemplified by an immunoperoxide assay for terminal deoxynucleotidyl transferase (TdT), a DNA polymerase enzyme found in lymphocyte cells of humans. Such an assay is marketed by the Coulter Immunology Division of Coulter Corporation, Hialeah, Florida which includes monoclonal antibody specific to TdT. TdT is particularly associated with T-cell differentiation. Elevated levels of the enzyme have been found to be symptomatic of certain human leukemias and has become a valuable marker for lymphoblastic neoplasms.

In performing a microscopic assay, a reliable control slide is desirable for maintaining the integrity of the analysis. Such a slide provides a standard against which to measure the sample cells being analyzed and assist the investigator in assuring that the reagents employed in preparing sample or specimen slides are functioning properly. Characteristic of such a control slide is the use of an intact cell specimen to serve as the control medium.

Significant obstacles have been encountered in preparing such a suitable control slide for TdT immunoassay because TdT is a fragile and sensitive enzyme, the expression of which is greatly affected by temperature, moisture and cell cycle. Heretofore, the control slide was prepared by "Cytospin" centrifuging approximately $5 \times 10^6$ normal lymphocytic cells at approximately 1200 rpm for approximately eight minutes at a desired dilution of phosphate buffered saline (PBS) to form a monolayer of cells on a slide. The cell monolayer then was used in the assay. However, conventional processing alters the monolayer cell response in the assay. Shipment to the investigators and storage in the laboratory at proper temperatures were required. For instance, the control slides could be fixed in absolute methanol and shipped at a storage temperature of 4° C. for up to 72 hours. Thereafter, the slides had to be stored at −70° C. until shipped or needed for use by the laboratory. Shipment conditions could not be assured; many laboratories did not have a storage facility functioning at −70° C.

Further experimentation with cytospin procedures established that "Cytospin" prepared slides could not be stored at 4° C. or room temperature and maintain the ability to obtain positive staining for TdT. Shipment and storage at such optimistic temperature conditions would be desirable advantages for such a control slide where intact cells functioned as the control medium.

Providing such a TdT control slide stable at room temperatures for prolonged periods of time required consideration of three (3) variables which impact on the TdT in the cells, to wit, fixation, dehydration and heat. Recognized procedures such as lyophilizing or freeze-drying and paraffin embedding processing were considered. Lyophilizing might resolve moisture problems whereas paraffin embedding might resolve the exposure to heat problem, but no assured resolution of the detrimental effect of moisture on the cell line. Elimination of excess moisture is essential in order to obtain adequate TdT staining. However, excessive or improper dehydration impairs the ability to store a TdT control slide for prolonged periods of time at reduced temperatures. Of course, the morphology of the cells must be maintained in the control slide. All of these factors, as well as others, such as using formalin as the fixative, were to be considered where the cell line was to be used as the control medium.

It was known to use certain fixation compounds and paraffin-embedding where cell tissue was used as the control medium. However, these conventional techniques impacted adversely on a marker such as TdT enzyme which is very sensitive and fragile. For instance, formalin used as a fixative impaired the molecules within lymphocyte cells required to maintain adequate TdT staining for control use. Graded ethyl alcohol generally used for dehydration treatment of cells gave rise to excessive or improper dehydration. Prior art paraffin-embedding used high melting point paraffin (58°–62° C.) whereas such a technique impacted adversely on TdT cell line.

This invention succeeds in providing a control slide for an immunoassay of the TdT type wherein a lyophilized intact cell segment preferably is paraffin-embedded on a slide to function as the control medium. The control slide of the invention is substantially stable and non-degrading with respect to its authenticity at ordinary room temperature. The invention comprises also the method of making such an advantageous control slide.

SUMMARY OF THE INVENTION

The present invention provides a stable, substantially permanent control slide for use in an immunoassay where the cell line functions as the preferred control medium and a method of making same. The actual glass slide or other appropriate substrate has mounted thereon a methanol-fixed and paraffin-supported section including at least a portion of intact cells, such as lymphocytes, for TdT enzyme assay, which portion is substantially stable and non-degrading with respect to its antigenicity at room temperature.

The method includes fixing the pellet of reference cells, prepared by centrifuging technique, with absolute methanol at room temperature and dehydrating the fixed cells with absolute, virgin methanol. The resulting pellet is then embedded in a block of low melting point paraffin in a mold, released from its mold and sectioned for staining and mounting on the slide.

DESCRIPTION OF THE PREFERRED EMBODIMENTS

The invention provides a stable, substantially permanent control slide for use in an immunoassay, such as an enzyme immunoassay for terminal deoxynucleotidyl transferase (TdT). The cell portions mounted on the slide include intact cellular structures which are well stained and which remain stable with respect to their antigenicity substantially permanently in room temperature storage.

Figure 1:
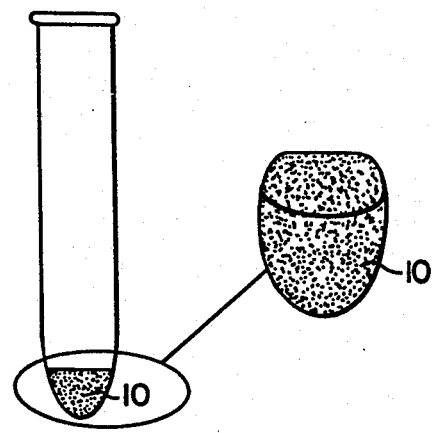
FIG. 1 is an enlarged perspective view of a pellet formed from a cell line according to the invention, including a view of the tube in which it is formed.
Figure 2:
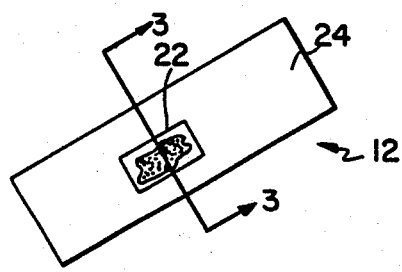
FIG. 2 is a perspective view of a representative control slide embodying the invention.
Figure 3:
FIG. 3 is a sectional view taken through the control slide along the line 3—3 of FIG. 2 and in the direction indicated generally.

FIG. 1 illustrates a representative cell pellet designated generally by the reference numeral 10. The pellet 10 is of the type prepared as an intermediate product in the preparation of the control slide 12 shown in FIG. 2. The pellet 10 is prepared by collecting in a centrifuge tube approximately $5 \times 10^6$ cells, such as lymphocyte cells in the case of a control slide for a TdT immunoassay, diluted to a dilution of $5.0 \times 10^6$ cell/ml in phosphate buffered saline (PBS). The collection of cells is spun down for approximately eight minutes at 1200 rpm to form the pellet 10. The pellet 10 with PBS then is treated, sectioned, mounted and stained according to the method diagrammatically illustrated in FIG. 4.

Figure 4:
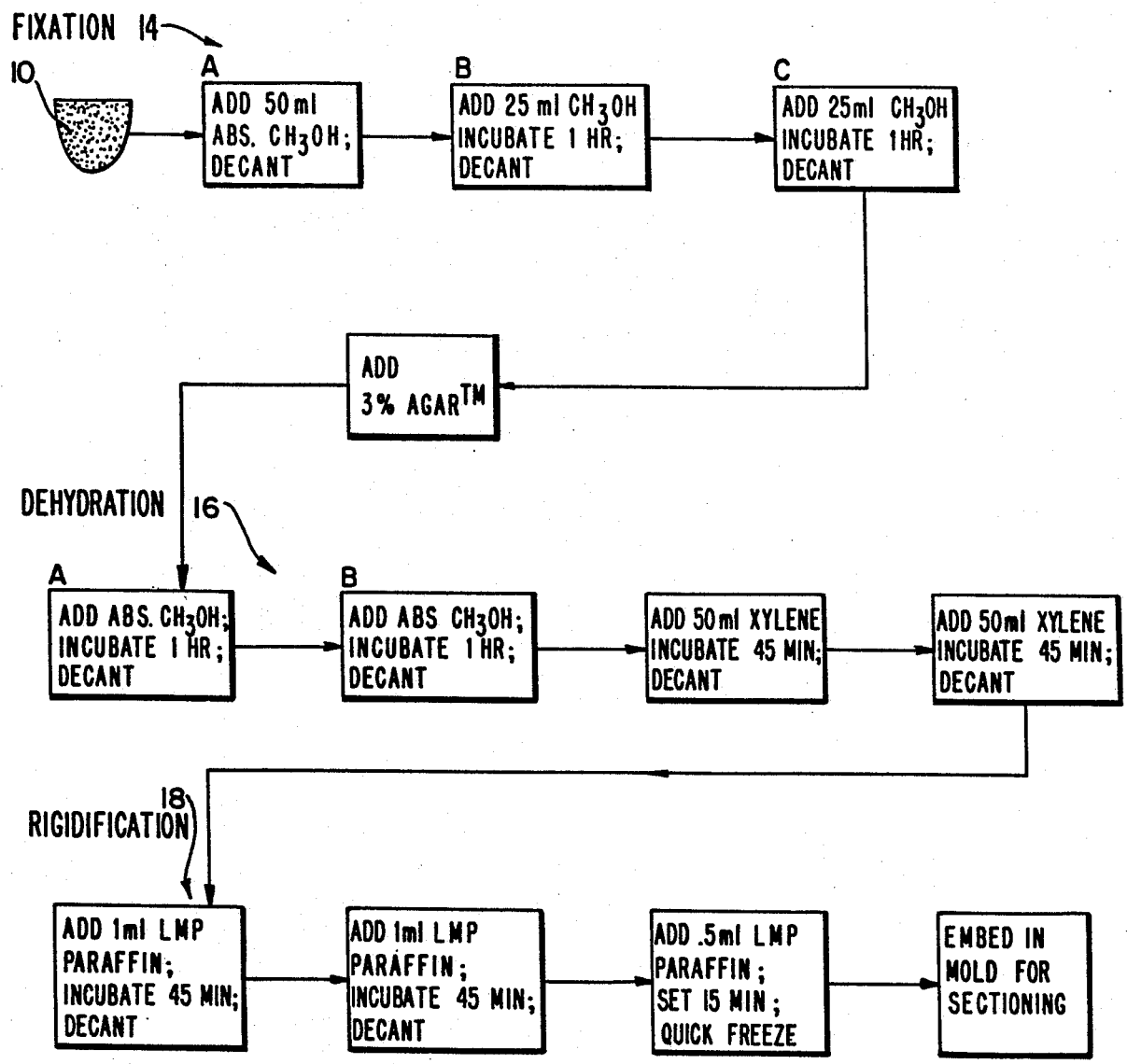
FIG. 4 is a schematic representation of the method embodying the invention for making the control slide of FIG. 2.

Referring to FIG. 4, the pellet 10 containing PBS first is fixed as represented by the reference character 14. The fixation procedure is as follows:

A. 50 milliliters of absolute methanol is added to the centrifuge tube and then withdrawn by decanting;

B. 25 ml of absolute methanol is added to the tube, agitated slightly and permitted to incubate for one (1) hour, after which the methanol is withdrawn by decanting;

C. 25 ml again is added, agitated slightly and incubated for one (1) hour, after which the methanol is removed, leaving the treated pellet.

Use of absolute methanol fixes the cells without compromising the integrity of the cytoplasm or membrane of cells. Further, fixation with absolute methanol was accomplished at room temperature whereas prior art fixation procedures using absolute methanol was performed at approximately 4° C.

After fixation of pellet 10, the pellet is removed to a small volume of aqueous 3% AGAR TM (DIFCO) and allowed to gel and form a semi-solid mass, which must be dehydrated. A proper degree of dehydration is required because moisture can effect the sensitivity of cells such as to damage the integrity of a cell line used for an immunoassay such as the TdT. Insufficient dehydration may interfere with proper TdT staining, for instance; excessive or improper dehydration throughout the cells can prevent the ability of the cells to store TdT, as is documented in the prior art.

Dehydration procedure is represented generally by the reference character 16 in FIG. 4, as follows:

A. The semi-solid mass prepared after fixation procedure 14, is transferred into fresh absolute methanol solution and permitted to incubate for one (1) hour; the methanol is withdrawn;

B. Fresh absolute methanol is added again for incubation of said mass for one (1) additional hour; the methanol then is withdrawn.

Upon completing this dehydration procedure, a substantially optimal quantity of moisture has been withdrawn without adverse trauma being suffered by the cells.

A procedure is now performed to remove the methanol from the said mass. Approximately 50 ml of Xylene is added and permitted to incubate for forty-five minutes. The Xylene is withdrawn by decanting and another 50 ml of Xylene is introduced and incubated again for forty-five minutes. The Xylene is then withdrawn by decanting. The successive Xylene treatments removes the methanol previously used.

The next procedure performed is represented by the reference character 18 which is designed to rigidify or set the pellet. Low melting point paraffin is added to the pellet in the amount of approximately 1 ml and permitted to incubate for about forty-five minutes. The paraffin is decanted and another 1 ml of low melting point paraffin is added to the pellet vessel and permitted to incubate for forty-five minutes. The paraffin is then decanted. The pellet is removed by adding 0.5 ml of low melting point paraffin and allowed to set or harden for about fifteen (15) minutes, and then quick-freezing with Freon of the bottom of the vessel so that the pellet embedded in paraffin can be popped out of the vessel.

Figure 1A:
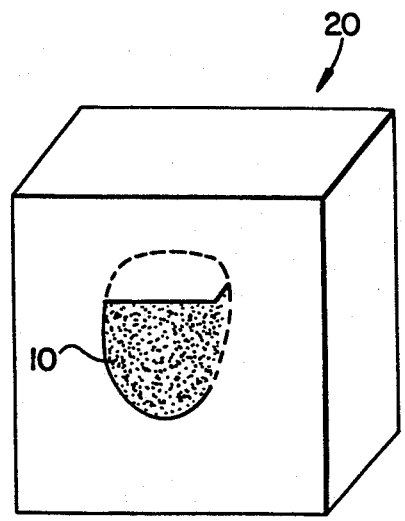
FIG. 1A is a perspective view of the molded block of paraffin in which the pellet of FIG. 1 is encased.

The paraffin embedded pellet is then placed in a contoured mold to harden into a block form 20 seen in FIG. 1A. It is this block form which permits sectioning into sections 22 of about 5 microns thick by means of a rotary microtone, for instance. A section 22 is placed on the slides 24 or other suitable substrate and dried for one (1) hour at approximately 58° C. The completed control slide is designated 12 in FIG. 2.

As has been explained, the temperature of the paraffin embedding medium is crucial to viability of the method embodying the invention. Use of heat is effectively reduced by using low melting point paraffin. Low melting point paraffin has a melting point of 52°–55° C. whereas so-called high melting point paraffin melts between 58°–62° C., which is commonly used under vacuum to embed cells in paraffin to form a rigid cell mass for sectioning in other laboratory procedures. The use of such high melting point paraffin generally causes trauma and heat damage to cells. Our use of low melting point paraffin successfully avoids cell trauma and damage, assists in maintaining proper cell morphology and antigenic expression in the immunoassay.

The low melting point paraffin used was an embedding medium identified by the trademark Paracut TM (TPN 132-118-0) produced by Technicon Instruments Corporation, Tarrytown, N.Y. Notably, vacuum induced impregnation is avoided and agitation of the paraffin/pellet combination is avoided.

After drying, the slides can be stored indefinitely at room temperature. Subsequent testing has shown that TdT cell lines prepared in this manner show excellent morphology, positive nuclear staining of TdT positive cells, no staining of TdT negative cells, and little or no cytoplasmic non-specific staining. All of these results compare most favorably with cytospun slides stored at −70° C. or those freshly prepared.

After drying, the slide is warmed in an oven at 56° C. for 15 minutes, placed in Xylene for 10 minutes to dewax and then placed in absolute methanol as the final fixing step. The absolute methanol preferably is changed after five minutes and left to incubate for another five minute period. Finally, the slide is placed in 3% $H_2O_2$ in methanol for 10 minutes, after which the slides can be stained. Staining procedures will be conventional for cells with slight modifications for TdT cell staining, for instance.

The control slide and method embodying the invention is equally effective for using TdT positive or TdT negative cell lines; prolonged room temperature storage is realized with both types of control slides. The control slide and method of the present invention also is viable for either the immunoperoxidase or immunofluorescence assay for TdT.

It is perceived that the invention can be adapted for the assay of other cell lines with equal advantages. For instance, assay of thymocytes using the monoclonal antibody specific to the T6 antigen may be feasible. The same may apply to certain cancer cell lines to which monoclonal antibodies have been developed. The procedures of the invention are not so severe as likely to damage a cell line.

We are not aware of any method involving TdT cell pellets or any other cell line pellets, that achieve the stability achieved by the control slide of the present invention. Current methodology, particularly with respect to TdT enzyme assay, recommends fresh cell preparations or cell preparations stored for less than two weeks at −20° C. or approximately −70° C.

It is contemplated that minor variations in practicing the invention may occur to persons skilled in the art, such as quantity of reagent used or length of incubation without departing from the spirit of the invention or the scope of the claims.

We claim:

1. A stable, substantially permanent immunoassay control slide in which a fixed cell line is a control medium comprising:
   a solid support substrate; and
   at least one intact fixed cell of a cell line embedded by being supported and enclosed in a low temperature melting point embedding medium comprising paraffin having a melting point within the approximate range of between 52–55° C. mounted on said substrate and being stained, the at least one intact fixed cell being substantially dehydrated and authentic in morphology, said at least one intact fixed cell being substantially permanently stable and non-degrading with respect to its antigenicity at ordinary room temperature, said cell line including TdT to be assayed.

2. the control slide of claim 1 in which said embedding medium and embedded cell is approximately five microns thick.

3. A control cell medium for use in an immunoassay in which a fixed cell line functions as the control, comprising:
   a. a collection of intact, chemically fixed cells of a cell line selected to function as a control for an immunoassay;
   b. said cells being in a pellet formation and embedded in a low temperature melting point paraffin having a melting point within the approximate range of between 52°–55° C., which is capable of being separated selectively into sections for use as the control;
   c. the cells in said formation further being stained, dehydrated, and authentic in their morphology;
   said control medium being characterized as substantially permanently stable and non-degrading with respect to its antigenicity at ordinary room temperature, said cell line including TdT to be assayed.

4. A stable, substantially permanent immunoassay control slide in which a fixed cell line is a control medium comprising:
   a solid support substrate; and
   at least one intact fixed cell of a cell line, which includes TdT to be assayed, embedded by being supported and enclosed in a low temperature melting point paraffin within the approximate range of between 52°–55° C. mounted on said substrate and being stained, the at least one intact fixed cell being substantially dehydrated and authentic in morphology, said at least one intact fixed cell being substantially permanently stable and non-degrading with respect to its antigenicity at ordinary room temperature.

* * * * *